United States Patent
Doering et al.

(10) Patent No.: US 11,026,877 B2
(45) Date of Patent: Jun. 8, 2021

(54) COSMETIC COMPOSITIONS FOR BLEACHING THE SKIN

(71) Applicant: Henkel AG & Co. KGaA, Duesseldorf (DE)

(72) Inventors: Thomas Doering, Dormagen (DE); Natascha Schevardo, Erkrath (DE); Melanie Giesen, Geldern (DE)

(73) Assignee: Henkel AG & Co. KGaA, Duesseldorf (DE)

( * ) Notice: Subject to any disclaimer, the term of this patent is extended or adjusted under 35 U.S.C. 154(b) by 121 days.

(21) Appl. No.: 15/373,926

(22) Filed: Dec. 9, 2016

(65) Prior Publication Data

US 2017/0087082 A1    Mar. 30, 2017

Related U.S. Application Data

(63) Continuation of application No. PCT/EP2015/061954, filed on May 29, 2015.

(30) Foreign Application Priority Data

Jun. 11, 2014  (DE) ..................... 10 2014 211 185.4

(51) Int. Cl.
| | |
|---|---|
| *A61K 8/9783* | (2017.01) |
| *A61K 8/67* | (2006.01) |
| *A61Q 19/02* | (2006.01) |
| *A61Q 15/00* | (2006.01) |
| *A61K 8/9789* | (2017.01) |
| *A61K 8/25* | (2006.01) |
| *A61K 8/49* | (2006.01) |

(52) U.S. Cl.
CPC ............... *A61K 8/676* (2013.01); *A61K 8/25* (2013.01); *A61K 8/4946* (2013.01); *A61K 8/4973* (2013.01); *A61K 8/9789* (2017.08); *A61Q 15/00* (2013.01); *A61Q 19/02* (2013.01)

(58) Field of Classification Search
None
See application file for complete search history.

(56) References Cited

U.S. PATENT DOCUMENTS

| | | | |
|---|---|---|---|
| 5,609,875 A | 3/1997 | Hadas | |
| 2006/0216254 A1 | 9/2006 | Majmudar et al. | |
| 2008/0152604 A1 | 6/2008 | Doering et al. | |
| 2010/0047296 A1* | 2/2010 | Banowski ............ | A61K 8/0229 424/401 |
| 2010/0247587 A1* | 9/2010 | Cebrian Puche ...... | A61K 8/498 424/401 |

FOREIGN PATENT DOCUMENTS

| | | | |
|---|---|---|---|
| CN | 102198055 A | * | 9/2011 |
| DE | 10333245 A1 | | 7/2005 |
| DE | 102004011968 A1 | | 9/2005 |
| GB | 2259014 B | | 3/1993 |
| KR | 20070112935 A | * | 11/2007 |
| WO | 99/55352 A1 | | 11/1999 |
| WO | 01/91715 A2 | | 12/2001 |

OTHER PUBLICATIONS

English translation of CN 102198055 retrieved from Espaceneton Jun. 18, 2019.*
PCT International Search Report (PCT/EP2015/061954) dated Jul. 20, 2015.
Database GNPD Mintel, "Whitening Night Cream", XP002742501, Database Accession No. 324341, 2004.
Database GNPD Mintel, "Spot Treatment Creme", XP002742498, Database Accession No. 429359, 2006.
Database GNPD Mintel, "BB Cream", XP002742500, Database Accession No. 1811286, 2012.
Database GNPD Mintel, "Night Cream", XP002742499, Database Accession No. 2137612, 2013.

* cited by examiner

Primary Examiner — Jessica Worsham
(74) Attorney, Agent, or Firm — P. Scott Smith

(57) ABSTRACT

The invention relates to a cosmetic composition for bleaching the skin, which includes a) at least one oily plant extract from the *Glycyrrhiza* genus and b) at least one ascorbic acid ester. The invention further relates to the cosmetic, non-therapeutic use of the cosmetic composition according to the invention to treat excessive pigmentation, pigmentation disorders, age spots, and/or post-inflammatory hyperpigmentation of the skin, and to a method for producing a cosmetic skin-bleaching composition in the form of an O/W or a W/O emulsion, wherein an oily extract from licorice roots is dissolved in the water phase by the addition of an ascorbic acid ester.

9 Claims, No Drawings

COSMETIC COMPOSITIONS FOR BLEACHING THE SKIN

FIELD OF THE INVENTION

The present invention generally relates to cosmetics, and more particularly relates to cosmetic compositions for skin bleaching, which include at least one oily plant extract from the *Glycyrrhiza* genus and at least one ascorbic acid ester.

The invention relates further to the cosmetic, nontherapeutic use of the cosmetic compositions to treat excessive pigmentation, pigment disorders, age spots, and/or post-inflammatory hyperpigmentation of the skin, and to a method for producing cosmetic skin-bleaching compositions in the form of emulsions, which include an oily plant extract from the *Glycyrrhiza* genus and at least one ascorbic acid ester.

BACKGROUND OF THE INVENTION

The pigmentation of skin occurs in melanocytes, which can be found, alongside basal cells, in the innermost layer of the epidermis as pigment-forming cells, occurring either individually or in clusters, depending on skin type. Melanocytes form melanosomes in which in turn melanin is formed. Melanin is formed increasingly by various chemical and/or physical influences, in particular by UV radiation. It is transported by keratinocytes into corneocytes (horny layer) and brings about a brownish to brown-black skin color. Melanin is formed as the end stage of an oxidative process, in which tyrosine is converted with the involvement of the enzyme tyrosinase via several intermediates to the brown to brown-black eumelanins (DHICA and DHI melanin) or with the participation of sulfur-containing compounds to the reddish pheomelanin.

Melanin formation, and thereby the skin and hair color, is subject to external influences and can also lead to unwanted phenomena apart from desired effects ("healthy tan"). Thus, e.g., UV radiation can lead to freckles. Abnormal pigmentation can also occur due to a genetic disposition, wound healing or scarring, or skin aging ("age spots").

Hormone-related disturbances can also be responsible for abnormal reactions of melanocytes and thereby for an increased accumulation of melanin in the skin, as a result of which unwanted brown spots develop on the skin.

It is therefore desirable to have available cosmetic compositions with which any "abnormal pigmentation" of the skin can be prevented, reduced, and/or eliminated lastingly and effectively.

Many bleaching compositions are known from the prior art.

White pigment-based compositions have the disadvantage that the skin-bleaching effect does not last long and often appears unnatural. Other active substances, such as, for example, reducing agents with hydroquinone or resorcinol structural units, produce excellent skin-bleaching effects but are poorly tolerated by skin and in part have a toxic effect on melanocytes. Permanent pigment changes can be the result.

Skin-bleaching agents, which include ascorbic acid or the physiologically acceptable derivatives or salts thereof and 8-hexadecene-1,16-dicarboxylic acid, sebacic acid, and/or azelaic acid, are proposed in DE 102005031482. The skin-bleaching agents can include further aqueous-alcoholic licorice extracts as a facultative active substance.

Cosmetic compositions for lightening skin spots are disclosed in DE 4227806, which include a flavonoid (for example, from licorice extract) and a DOPA-quinone-reducing agent (for example, ascorbic acid or certain ascorbyl esters).

Both compositions are based on aqueous and/or aqueous-alcoholic licorice extracts or on water-soluble flavonoids in combination with ascorbic acid (derivatives).

Tests with various plant extracts showed that oily licorice extracts are far superior to the aqueous or aqueous-alcoholic licorice extracts in regard to their skin-bleaching action, which is why it is desirable to use oily licorice extracts in cosmetic skin-bleaching compositions.

Upon incorporation of oily licorice extracts into cosmetic emulsions, the preferred application form for skin care agents, these exhibited an insufficient solubility in the aqueous phase, however, as a result of which both the visual appearance (high turbidity of the aqueous phase) and the stability of the compositions were negatively affected. This problem could also not be resolved by the addition of solubilizers.

The object of the present invention was to incorporate oily licorice extracts into cosmetic compositions for topical application and to stabilize them therein. The compositions should produce a skin-bleaching effect on excessively or abnormally pigmented skin and be very well tolerated by skin.

It was found completely surprisingly that the aforesaid object can be achieved by a combination of an oily licorice extract with at least one ascorbic acid ester.

Furthermore, other desirable features and characteristics of the present invention will become apparent from the subsequent detailed description of the invention and the appended claims, taken in conjunction with this background of the invention.

BRIEF SUMMARY OF THE INVENTION

A cosmetic composition for skin bleaching, including at least one oily plant extract from the *Glycyrrhiza* genus and at least one ascorbic acid ester.

A method for producing a cosmetic skin-bleaching composition in the form of an O/W or a W/O emulsion, in which an oily extract from licorice roots is dissolved in the aqueous phase by the addition of an ascorbic acid ester.

DETAILED DESCRIPTION OF THE INVENTION

The following detailed description of the invention is merely exemplary in nature and is not intended to limit the invention or the application and uses of the invention. Furthermore, there is no intention to be bound by any theory presented in the preceding background of the invention or the following detailed description of the invention.

A first subject of the invention is a cosmetic composition for skin bleaching, which includes a) at least one oily plant extract from the *Glycyrrhiza* genus and b) at least one ascorbic acid ester.

The compositions of the invention have a number of advantages:

they are easy to produce and themselves can be readily formulated as an emulsion, without turbidity, separation, and/or stability problems arising, oily licorice extracts can be completely dissolved in the aqueous phase by the addition of the ascorbic acid ester, as a result of which products can be obtained that are attractive visually and also in terms of application technology, the compositions have an excellent skin-bleaching action and are suitable for preventing and/or for treating excessive pigmentation, pigmentation disorders, age spots, and/or post-inflammatory hyperpigmentation of the skin, the active substance combination of an oily licorice extract and an ascorbic acid ester acts synergistically in regard to skin bleaching, the compositions are very well tolerated by skin, good bioavailability of the active substances.

An "oily" extract according to the invention is taken to mean that the licorice extract is present dissolved in a preferably liquid organic compound, water-insoluble at room temperature.

"Water-insoluble" is taken to mean that a maximum of 1 g, preferably a maximum of 0.5 g, more preferably a maximum of 0.1 g, and particularly preferably a maximum of 0.01 g of the organic compound dissolve in 1 L of water at room temperature.

"Organic compounds" are preferably understood to be synthetic, mineral, or natural oils (triglycerides), which will be described in greater detail later in the application.

"Skin bleaching" is taken to mean the change in skin color caused by a reduced formation of melanin.

The oily plant extract from the licorice genus (*Glycyrrhiza*) can be produced in principle from all parts such as the leaves, flowers, seeds, and/or the roots of licorice.

Especially suitable in the context of the present invention, however, are the oily extracts from the roots of *Glycyrrhiza glabra* (licorice roots), because they exhibit the strongest synergistic skin-bleaching effect in conjunction with the ascorbic acid ester.

In a first preferred embodiment, the cosmetic compositions for skin bleaching therefore include an oily extract from the roots of *Glycyrrhiza glabra* (licorice roots).

All physiologically acceptable, synthetic, mineral, or natural oils may be used in principle as a suitable oily extraction medium for the licorice roots. Preferred extracting agents, however, are the so-called ester oils.

Ester oils are understood to be the esters of straight-chain or branched, saturated or unsaturated $C_6$-$C_{30}$ carboxylic acids with straight-chain or branched, saturated or unsaturated $C_2$-$C_{30}$ alcohols. The monoesters of saturated or unsaturated $C_8$-$C_{24}$ carboxylic acids with straight-chain or branched alcohols having 2 to 24 C atoms are preferred. Particularly preferred are monoesters of saturated or unsaturated $C_{10}$-$C_{22}$ carboxylic acids with straight-chain or branched, preferably branched, $C_3$-$C_{10}$ alcohols such as, for example, isopropyl myristate (Rilanit® IPM), isononanoic acid-$C_{16-18}$ alkyl ester (Cetiol® SN), 2-ethylhexyl palmitate (Cegesoft® 24), stearic acid-2-ethylhexyl ester (Cetiol® 868), cetyl oleate, glycerol tricaprylate, coconut fatty alcohol caprinate/caprylate (Cetiol® LC), n-butyl stearate, oleyl erucate (Cetiol® J 600), isopropyl palmitate (Rilanit® IPP), oleyl oleate, lauric acid hexyl ester (Cetiol® A), di-n-butyl adipate (Cetiol® B), myristyl myristate (Cetiol® MM), cetearyl isononanoate (Cetiol® SN), and oleic acid decyl ester (Cetiol® V).

Isopropyl myristate, isopropyl palmitate, and 2-ethylhexyl palmitate are very particularly preferred; isopropyl myristate is particularly preferred.

In a second preferred embodiment, the cosmetic compositions for skin bleaching include an isopropyl myristate extract from the roots of *Glycyrrhiza glabra* (licorice roots).

An oily plant extract, suitable for the compositions of the invention, from the licorice genus (*Glycyrrhiza*) is obtainable, for example, under the trade name "Liquorice Herbasol® Extract IPM" from the company Cosmetochem.

The oily plant extracts from the licorice genus preferably include a licorice active substance content of 0.001 to 90% by weight, more preferably of 0.002 to 70% by weight, particularly preferably of 0.005 to 50% by weight, very particularly preferably of 0.01 to 30% by weight, and in particular of 0.05 to 10% by weight, the quantitative data referring to the total weight of the oily plant extract.

The cosmetic compositions include the oily plant extract from the licorice genus preferably in an amount of 0.01 to 5% by weight, more preferably of 0.05 to 4% by weight, particularly preferably of 0.1 to 3% by weight, and in particular of 0.2 to 2% by weight, the quantitative data referring to the total weight of the cosmetic composition.

According to a preferred embodiment, 0.01 to 5% by weight, more preferably of 0.05 to 4% by weight, particularly preferably of 0.1 to 3% by weight, and in particular of 0.2 to 2% by weight of Liquorice Herbasol® Extract IPM from the company Cosmetochem are employed in the compositions of the invention; the quantitative data in this case refer to the total weight of the cosmetic compositions.

In a third preferred embodiment, the cosmetic compositions of the invention include an ascorbic acid ester, which is selected from compounds of the following formula (I),

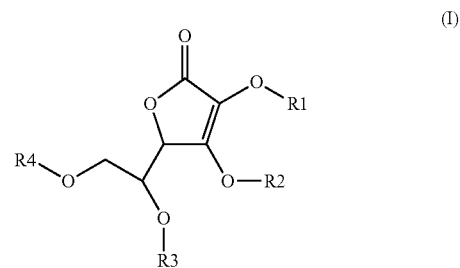

(I)

in which one to four of the groups R1 to R4 stand for the group —C(O)—R and the other groups optionally stand for hydrogen; and R stands for a straight-chain or branched, saturated or unsaturated alk(en)yl group having 8 to 24, preferably 10 to 20, and in particular 13 to 17 carbon atoms.

It was found that the synergistic skin-bleaching effect can be enhanced, if specific ascorbic acid esters are used in combination with oily licorice extracts. Particularly preferred esters according to the formula (I) are selected from ascorbyl palmitate, ascorbyl isopalmitate, ascorbyl tetraisopalmitate, ascorbyl stearate, ascorbyl isostearate, ascorbyl oleate, and/or ascorbyl linoleate.

Ascorbyl tetraisopalmitate is particularly preferred, because the combination of ascorbyl tetraisopalmitate with oily licorice extracts resulted in the greatest synergistic skin-bleaching effect. Moreover, the oily licorice extracts dissolved especially well in the aqueous phase of emulsions, if ascorbyl tetraisopalmitate was added to the aqueous phase.

In another preferred embodiment, the cosmetic compositions therefore include as ascorbic acid esters according to the formula (I) at least one compound, selected from ascorbyl palmitate, ascorbyl isopalmitate, ascorbyl tetraisopalmitate, ascorbyl stearate, ascorbyl isostearate, ascorbyl oleate, and/or ascorbyl linoleate.

In a particularly preferred embodiment, the cosmetic compositions include ascorbyl tetraisopalmitate.

The at least one ascorbic acid ester is used in the cosmetic compositions preferably in a weight proportion of 0.005 to 1% by weight in terms of the total weight of the cosmetic composition, particularly preferably of 0.0075 to 0.5% by weight, and in particular of 0.01 to 0.2% by weight.

It was found that the aforesaid synergistic skin-bleaching effect occurs especially greatly, if the active substances a) and b) are used in a specific weight ratio in the cosmetic compositions.

In a fourth preferred embodiment, the cosmetic compositions of the invention include components a) and b) therefore preferably in a weight ratio a):b) of 20:1 to 1:2, more preferably of 17.5 to 1:1, particularly preferably of 15:1 to 2:1, very particularly preferably of 12.5:1 to 5:1, and in particular of 10:1 to 7.5:1.

The agents of the invention have an excellent skin tolerance and are capable not only of lightening pigmented skin but moreover of giving it smoothness, suppleness, and softness.

When potentially irritated skin is treated, such as, for example, skin after shaving, unclean skin and/or skin affected by acne and/or if post-inflammatory hyperpigmentation is present, it can be advantageous, however, if the cosmetic compositions of the invention include further an active substance that soothes the skin.

Preferred skin-soothing active substances, which can be used in the cosmetic compositions of the invention, are, for example, selected from farnesol, allantoin, alpha-bisabolol, and/or alpha-lipoic acid, particularly preferably from allantoin and/or alpha-bisabolol and in particular preferably from allantoin.

The skin-soothing active substance(s) can be used in the agents of the invention preferably in an amount of 0.01 to 5% by weight, more preferably of 0.05 to 3% by weight, particularly preferably of 0.075 to 2% by weight, and in particular of 0.1 to 1% by weight, the quantitative data referring to the total weight of the cosmetic agent.

In another preferred embodiment, the cosmetic compositions of the invention include further allantoin in a weight proportion (based on the total weight of the composition) of 0.01 to 5% by weight, preferably of 0.05 to 3% by weight, particularly preferably of 0.075 to 2% by weight, and in particular of 0.1 to 1% by weight.

The preparations of the invention can be present in principle in the form of a solution, an emulsion of the water-in-oil (W/O) or oil-in-water (O/W) type, a multiple emulsion of the water-in-oil-in-water (W/O/W) or oil-in-water-in-oil (O/W/O) type, a hydrodispersion or lipid dispersion, a gel, a solid stick, and/or an aerosol.

Particularly preferably the compositions of the invention are present in the form of an emulsion.

In another preferred embodiment of the invention, the compositions of the invention are present in the form of a solution, an emulsion of the water-in-oil (W/O) or oil-in-water (O/W) type, a multiple emulsion of the water-in-oil-in-water (W/O/W) or oil-in-water-in-oil (O/W/O) type, a hydrodispersion or lipid dispersion, a gel, a solid stick, and/or an aerosol, particularly preferably in the form of an emulsion.

In a particularly preferred embodiment, the compositions of the invention are present in the form of a water-in-oil emulsion (W/O emulsion).

Emulsions in the context of the present invention can be present, for example, in the form of creams, lotions, and/or cosmetic milks and include apart from the aforesaid active substances more preferably fats, oils, waxes, and/or other fatty substances, as well as water and one or more emulsifiers.

The oil phase is present in the preferred emulsions of the invention preferably in a weight proportion of 1-60% by weight in terms of the total weight of the emulsion, particularly preferably of 10-50% by weight, and exceptionally preferably of 15-35% by weight.

The emulsifier(s) is(are) not included either in the oil phase or in the aqueous phase. In a preferred embodiment, the oil phase consists of at least 90% by weight of an oil component that is liquid at 20° C.

Preferred oil components that can be used in the preferred emulsions of the invention are, for example, selected from:

volatile silicone oils, which may be cyclic, such as, e.g., octamethylcyclotetrasiloxane, decamethylcyclopentasiloxane, and dodecamethylcyclohexasiloxane, and mixtures thereof, as they are included, e.g., in the commercial products DC 244, 245, 344, and 345 from Dow Corning, or linear, e.g., hexamethyldisiloxane (L 2), octamethyltrisiloxane (L 3), decamethyltetrasiloxane (L 4), any two-component and three-component mixtures of L 2, L 3, and/or L 4, as they are included, e.g., in the commercial products DC 2-1184, Dow Corning® 200 (0.65 cSt), and Dow Corning® 200 (1.5 cSt) from Dow Corning;

nonvolatile higher-molecular-weight linear dimethylpolysiloxanes, commercially available, e.g., under the name Dow Corning® 190, Dow Corning® 200 Fluid with viscosities in the range of 5-100 cSt, preferably 5-50 cSt, or also 5-10 cSt, and Baysilon® 350 M;

the esters of linear or branched, saturated or unsaturated fatty alcohols having 2 to 30 carbon atoms with linear or branched, saturated or unsaturated fatty acids having 2 to 30 carbon atoms, which may be hydroxylated. These include 2-ethylhexyl palmitate (e.g., Cegesoft® C 24), hexyldecyl stearate (Eutanol® G 16), hexyldecyl laurate, isodecyl neopentanoate, isononyl isononanoate, 2-ethylhexyl stearate, isopropyl myristate, isopropyl palmitate, isopropyl stearate, isopropyl isostearate, isopropyl oleate, isooctyl stearate, isononyl stearate, isocetyl stearate, isononyl isononanoate, isotridecyl isononanoate, cetearyl isononanoate, 2-ethylhexyl laurate, 2-ethylhexyl isostearate, 2-ethylhexyl cocoate, 2-octyldodecyl palmitate, butyloctanoic acid-2-butyl octanoate, diisotridecyl acetate, n-butyl stearate, n-hexyl laurate, n-decyl oleate, oleyl oleate, oleyl erucate, erucyl oleate, erucyl erucate, and ethylene glycol dioleate and dipalmitate;

the benzoic acid esters of linear or branched $C_{8-22}$ alkanols, e.g., the commercial products Finsolv® TN ($C_{12}$-$C_{15}$ alkyl benzoate), Finsolv® SB (isostearyl benzoate), and Finsolv® EB (ethylhexyl benzoate);

the $C_8$-$C_{22}$ fatty alcohol esters of monovalent or polyvalent $C_2$-$C_7$ hydroxycarboxylic acids, in particular the esters of glycolic acid, lactic acid, malic acid, tartaric acid, citric acid, and salicylic acid. Esters of this kind based on linear $C_{12/15}$ alkanols, e.g., $C_{12}$-$C_{15}$ alkyl lactate, and of $C_{12/13}$ alkanols branched in the 2-position, e.g., di-$C_{12}$-$C_{13}$ alkyl malate, may be obtained under the trademark Cosmacol® from the company Nordmann, Rassmann GmbH & Co, Hamburg, in particular the commercial products Cosmacol® EMI, Cosmacol® ESI, and Cosmacol® ETI;

the adducts of ethylene oxide and/or propylene oxide with monohydric or polyhydric $C_{3-20}$ alkanols such as butanol, butanediol, myristyl alcohol, and stearyl alcohol, e.g., PPG-14 butyl ether (Ucon Fluid®), PPG-9 butyl ether (Breox® B25), PPG-10 butanediol (Macol® 57), PPG-3 myristyl ether (Witconol® APM), and PPG-15 stearyl ether (Arlamol® E);

liquid paraffin oils, isoparaffin oils, e.g., the commercial products of the Permethyl® series, in particular isododecane, isohexadecane, and isoeicosane;

synthetic hydrocarbons such as polyisobutene or polydecene, and alicyclic hydrocarbons, e.g., the commercial product 1,3-di-(2-ethylhexyl)cyclohexane (Cetiol® S);

the branched saturated or unsaturated fatty alcohols having 6-30 carbon atoms. These alcohols are often also referred to as "Guerbet alcohols," since they are obtainable by the Guerbet reaction. Particularly preferred alcohol oils are, for example, hexyldecanol (Eutanol® G), octyldodecanol, and 2-ethylhexyl alcohol;

mixtures of Guerbet alcohols and Guerbet alcohol esters, e.g., the commercial product Cetiol® PGL (hexyldecanol and hexyldecyl laurate);

the symmetrical, asymmetrical, or cyclic esters of carbonic acid with fatty alcohols, for example, glycerol carbonate, dicaprylyl carbonate (Cetiol® CC);

triglycerides of linear or branched, saturated or unsaturated, optionally hydroxylated $C_{8-30}$ fatty acids. The use of natural oils, e.g., soybean oil, cottonseed oil, sunflower oil, palm oil, palm kernel oil, linseed oil, almond oil, castor oil, corn oil, olive oil, rapeseed oil, sesame oil, thistle oil, wheat germ oil, peach kernel oil, and the liquid components of coconut oil and the like, can be particularly suitable. Also suitable, however, are synthetic triglyceride oils, in particular capric/caprylic triglycerides, e.g., the commercial products Myritol® 318, Myritol® 331 (Cognis), or Miglyol® 812 (Hills), as well as glyceryl triisostearin and the commercial products Estol® GTEH 3609 (Uniqema) or Myritol® GTEH (Cognis);

dicarboxylic acid esters of linear or branched $C_2$-$C_{10}$ alkanols, in particular diisopropyl adipate, di-n-butyl adipate, di-(2-ethylhexyl) adipate, dioctyl adipate, diethyl-/di-n-butyl/dioctyl sebacate, diisopropyl sebacate, dioctyl malate, dioctyl maleate, dicaprylyl maleate, diisooctyl succinate, di-2-ethylhexyl succinate, and di-(2-hexyldecyl) succinate;

di-n-alkyl ethers having a total of 12 to 36, in particular 12 to 24 C atoms, e.g., di-n-octyl ether (Cetiol® OE), di-n-n-hexyl-n-octyl ether, and n-octyl-n-decyl ether.

Particularly preferred oils are the silicone oils and esters of linear or branched, saturated or unsaturated fatty alcohols having 2 to 30 carbon atoms with linear or branched, saturated or unsaturated fatty acids having 2-30 carbon atoms, primarily decamethylcyclopentasiloxane and dodecamethylcyclohexasiloxane, hexamethyldisiloxane (L 2), octamethyltrisiloxane (L 3), and decamethyltetrasiloxane (L 4), as well as any two-component and three-component mixtures of L 2, L 3, and/or L 4, volatile and nonvolatile linear silicone oils from the Dow Corning 200 Fluid series having viscosities of 0.65, 1.0, 1.5, and 5 cSt, the ester oils 2-ethylhexyl palmitate, hexyldecyl laurate, 2-ethylhexyl stearate, isopropyl myristate, isopropyl palmitate, and 2-ethylhexyl laurate, the benzoic acid esters of linear or branched $C_{8-22}$ alkanols, in particular the commercial product Finsolv®, esters of linear or branched, saturated or unsaturated fatty alcohols having 2 to 30 carbon with linear or branched, saturated or unsaturated fatty acids having 2-20 carbon atoms, $C_{12}$-$C_{15}$ alkyl lactate, di-$C_{12}$-$C_{13}$ alkyl malate, PPG-14 butyl ether, the commercial products of the Permethyl® series, in particular isododecane, isohexadecane, and isoeicosane, as well as polyisobutene and polydecenes, and mixtures of the aforesaid components.

In another preferred embodiment, the cosmetic compositions of the invention include furthermore at least one silicone in a weight proportion (based on the total weight of the composition) of 0.05 to 20% by weight, preferably of 0.1 to 17.5% by weight, particularly preferably of 0.25 to 15% by weight, and in particular of 0.5 to 12.5% by weight.

It may also be preferred for some embodiments of the compositions of the invention to use mixtures of the aforesaid oils. In this regard, in particular mixtures of two oil component types, e.g., a volatile silicone oil and an ester oil, are preferred. Oil mixtures that include at least one volatile cyclic and/or a linear silicone oil are particularly preferred. Oil mixtures that include predominantly, i.e., in a proportion of more than 50% by weight, based on the oil mixture, at least one volatile cyclic and/or linear silicone oil are exceptionally preferred. Preferred, furthermore, are oil mixtures that include 60-95% by weight, particularly preferably 70-90% by weight of at least one volatile cyclic and/or linear silicone oil in combination with 5-40% by weight, particularly preferably 10-30% by weight of at least one ester oil, in particular one of the aforesaid ester oils, based in each case on the weight of the oil mixture.

The aqueous phase is present in the emulsions preferred according to the invention preferably in a weight proportion of 40-99% by weight in terms of the total weight of the emulsion, particularly preferably of 50-90% by weight, and exceptionally preferably of 60-85% by weight.

The aqueous phase includes preferably according to the invention water and all water-soluble ingredients, with the exception of the emulsifiers.

Preferred cosmetic compositions in the form of emulsions are characterized by a water content of 20-70% by weight, preferably 25-65% by weight, and particularly preferably 30-60% by weight, based in each case on the total weight of the emulsion.

The emulsions preferred according to the invention preferably include furthermore at least one emulsifier, preferably a water-in-oil emulsifier. The at least one emulsifier is preferably included in an amount of 0.5-10% by weight, particularly preferably 1.0-7.5% by weight, and in particular of 1.5-5% by weight in the emulsions, the quantitative data referring to the total weight of the emulsions.

Particularly preferred emulsifiers can be selected from:

poly-($C_2$-$C_3$) alkylene glycol-modified silicones with the INCI names PEG-x Dimethicone (with x=2-20, preferably 3-17, particularly preferably 11-12), bis-PEG-y Dimethicone (with y=3-25, preferably 4-20), PEG/PPG a/b Dimethicone (where a and b independently of one another stand for numbers from 2-30, preferably 3-30, and particularly preferably 12-20, in particular 14-18), bis-PEG/PPG-c/d Dimethicone (where c and d independently of one another stand for numbers from 10-25, preferably 14-20, and particularly preferably 14-16), and bis-PEG/PPG-e/f PEG/PPG g/h Dimethicone (where e, f, g, and h independently of one another stand for numbers from 10-20, preferably 14-18, and particularly preferably 16). Particularly preferred are PEG/PPG-18/18 Dimethicone, which is commercially available in a 1:9 mixture with cyclomethicone as DC 3225 C or DC 5225 C, PEG/PPG-4/12 Dimethicone, which is obtainable under the name Abil B 8852, and bis-PEG/PPG-14/14 Dimethicone, which is commercially available in a mixture with cyclomethicone as Abil EM 97 (Goldschmidt), bis-PEG/PPG-20/20 Dimethicone, which is obtainable under the name Abil B 8832, PEG/PPG-5/3 Trisiloxane (Silsoft 305), and PEG/PPG-20/23 Dimethicone (Silsoft 430 and Silsoft 440). Additional emulsifiers preferred according to the invention are poly-($C_2$-$C_3$) alkylene glycol-modified silicones that are hydrophobically modified with $C_4$-$C_{18}$ alkyl groups, particularly preferably Cetyl PEG/PPG-10/1 Dimethicone (previously: Cetyl Dimethicone Copolyol, obtainable as Abil EM 90 or in a mixture of polyglyceryl-4 isostearate, Cetyl PEG/PPG-10/1 Dimethicone, and hexyl laurate, under the trade name Abil WE 09), further Alkyl Methicone Copolyols and Alkyl Dimethicone Ethoxy Glucosides;

substances of the general formula A-O—(CHR1-X—CHR2-O-)a-A', where A and A' represent the same or different hydrophobic organic groups, "a" represents a number from 1 to 100, preferably 2 to 60, in particular 5 to 40, X represents a single bond or the group CHOR3, R1 and R2 represent a hydrogen atom or a methyl group and are selected so that both groups do not simultaneously represent methyl, and R3 represents a hydrogen atom or a branched or unbranched, saturated or unsaturated alkyl or acyl group having 1 to 20 carbon atoms;

it is particularly preferred if the groups A and A' are selected from the group of branched and unbranched, saturated and unsaturated alkyl and acyl groups and hydroxyacyl groups having 10 to 30 carbon atoms, and furthermore from the group of hydroxyacyl groups joined to one another via ester functions, according to the scheme: OOC—R"—CR'H—(OOC—R"—CR'H) b-OOC—R"—CHR', where R' is selected from the group of branched and unbranched alkyl groups having 1 to 20 carbon atoms and R" is selected from the group of branched and unbranched alkylene groups having 1 to 20 carbon atoms, and b can assume values from 0 to 200;

saturated alcohols having 8-24 C atoms, in particular having 16-22 C atoms, e.g., cetyl alcohol, stearyl alcohol, arachidyl alcohol, or behenyl alcohol or mixtures of said alcohols such as those obtained upon industrial hydrogenation of vegetable and animal fatty acids;

ethoxylated alcohols and carboxylic acids having 8-24 C atoms, in particular having 16-22 C atoms, such as, for example, Steareth-2 or Steareth-21;

propoxylated alcohols and carboxylic acids having 8-24 C atoms, in particular having 16-22 C atoms;

partial esters of a polyol having 3-6 C atoms and saturated and/or unsaturated, branched and/or unbranched fatty acids having 8-24, in particular 12-18 C atoms. Such partial esters are, e.g., the monoglycerides of palmitic acid, stearic acid, and oleic acid, the sorbitan mono- and/or diesters, in particular those of myristic acid, palmitic acid, stearic acid, or of mixtures of said fatty acids. Also to be mentioned here are the monoesters of trimethylolpropane, erythritol, or pentaerythritol, and saturated fatty acids having 14-22 C atoms. The technical monoesters that are obtained by esterification of 1 mol of polyol with 1 mol of fatty acid and represent a mixture of monoesters, diesters, triesters, and if applicable unesterified polyol, are also usable;

polyglycerol esters of saturated and/or unsaturated, branched and/or unbranched alkanecarboxylic acids with a chain length of 8-24, in particular 12-18 C atoms, having up to 10 glycerol units, preferably up to 3 glycerol units, and a degree of esterification of 1-10, preferably 1-5;

mono- and/or polyglycerol ethers of saturated and/or unsaturated, branched and/or unbranched alcohols with a chain length of 8-30, in particular 12-18 C atoms, having up to 10 glycerol units, preferably up to 3 glycerol units, and a degree of etherification of 1-10, preferably 1-5;

propylene glycol esters of saturated and/or unsaturated, branched and/or unbranched alkanecarboxylic acids with a chain length from 8-24, in particular 12-18 C atoms;

methylglucose esters of saturated and/or unsaturated, branched and/or unbranched alkanecarboxylic acids with a chain length of 8-24, in particular 12-18 C atoms;

polyglycerol methylglucose esters of saturated and/or unsaturated, branched and/or unbranched alkanecarboxylic acids with a chain length of 8-24, in particular 12-18 C atoms. It can be advantageous according to the invention to utilize products with a low degree of ethoxylation (3-5 EO) and/or propoxylation, for example, polyethoxylated hydrogenated or non-hydrogenated castor oil or ethoxylated cholesterol.

Very particularly preferred emulsifiers are glyceryl lanolate, glyceryl monostearate, glyceryl distearate, glyceryl monoisostearate, glyceryl monomyristate, glyceryl monooleate, diglyceryl monostearate, glyceryl monolaurate, glyceryl monocaprinate, glyceryl monocaprylate, diglyceryl monoisostearate, diglyceryl diisostearate, propylene glycol monostearate, propylene glycol monolaurate, sorbitan monoisostearate, sorbitan monolaurate, sorbitan monocaprylate, sorbitan sesquistearate, sorbitan monoisooleate, sucrose distearate, cetyl alcohol, stearyl alcohol, arachidyl alcohol, behenyl alcohol, isobehenyl alcohol, 2-ethylhexylglycerol ether, selachyl alcohol, chimyl alcohol, batyl alcohol, polyethylene glycol (2) stearyl ether (Steareth-2), polyethylene glycol (21) stearyl ether (Steareth-21), glyceryl sorbitan stearate, polyglyceryl-4 isostearate, polyglyceryl-2 sesquiisostearate, PEG-7 Hydrogenated Castor Oil, isostearyl diglyceryl succinate, PEG-5 cholesteryl ether, PEG-30 dipolyhydroxystearate, decaglyceryl heptaoleate, polyglyceryl-3 diisostearate, PEG-8 distearate, diglycerol dipolyhydroxystearate, glycerol isostearate, sorbitan isostearate, polyglyceryl-3 methylglucose distearate, polyethoxylated hydrogenated or non-hydrogenated castor oil, ethoxylated cholesterol, PEG-2 stearate, PPG-15 stearyl ether, PEG/PPG-18/18 Dimethicone, PEG-45/dodecylglycol copolymer, PEG-22/dodecylglycol copolymer, and Methoxy PEG-22/Dodecyl Glycol Copolymer.

It is very particularly preferred if combinations of the aforesaid emulsifiers, in particular a combination of two emulsifiers, are used. It can also be advantageous according to the invention to use at least one W/O emulsifier in combination with at least one O/W emulsifier.

The emulsions preferred according to the invention preferably include furthermore ethanol. Ethanol is preferred, for example, when the refreshing effect evoked by the high water content of the compositions of the invention is to be further enhanced.

Ethanol is used in the emulsions preferred according to the invention preferably in amounts of 0-10% by weight, particularly preferably 0.01-7.5% by weight, and exceptionally preferably of 0.1-5% by weight, based in each case on the total emulsion.

The emulsions preferred according to the invention preferably include furthermore at least one water-soluble polyol, selected from the water-soluble polyhydric $C_2$-$C_9$ alkanols with 2-6 hydroxyl groups and water-soluble polyethylene glycols with 3-20 ethylene oxide units, and mixtures thereof.

These components are preferably selected from 1,2-propylene glycol, 2-methyl-1,3-propanediol, glycerol, butylene glycols such as 1,2-butylene glycol, 1,3-butylene glycol, and 1,4-butylene glycol, pentylene glycols, hexanediols such as 1,2-hexanediol, 1,6-hexanediol, hexanetriols such as 1,2,6-hexanetriol, 1,2-octanediol, 1,8-octanediol, dipropylene glycol, tripropylene glycol, diglycerol, triglycerol, erythritol, sorbitol, and mixtures of the aforesaid substances. Preferred water-soluble polyethylene glycols are selected from PEG-3, PEG-4, PEG-6, PEG-7, PEG-8, PEG-9, PEG-10, PEG-12, PEG-14, PEG-16, PEG-18, and PEG-20, and mixtures thereof, PEG-3 to PEG-8 being particularly preferred. Sugars and certain sugar derivatives, such as fructose, glucose, maltose, maltitol, mannitol, inositol, sucrose, trehalose, and xylose can also be preferred according to the invention.

1,2-Propylene glycol, glycerol, 1,3-butylene glycol, diglycerol, triglycerol, dipropylene glycol, and tripropylene glycol are particularly preferred.

1,2-Propylene glycol and glycerol are particularly preferred. The water-soluble polyol is used in the emulsions preferred according to the invention preferably in amounts of 0.01-30% by weight, particularly preferably 0.1-27.5% by weight, and exceptionally preferably of 0.5-25% by weight, based in each case on the total emulsion.

It was found that inflammatory reactions can occur on the skin in the axillary region due to frequent shaving, which can result in unwanted skin discolorations. To prevent these discolorations or to reduce or eliminate them, it is advantageous in another embodiment, if the compositions of the invention are formulated as a deodorant or antiperspirant composition.

In a fifth preferred embodiment, the compositions of the invention therefore include furthermore at least one active antiperspirant substance in a weight proportion (based on the total weight of the composition) of 3 to 40% by weight, preferably of 5 to 35% by weight, particularly preferably of 7.5 to 30% by weight, and in particular of 10 to 25% by weight.

Within this embodiment, the compositions of the invention include at least one water-soluble active antiperspirant substance such as, for example, the water-soluble astringent inorganic and organic salts of the aluminum, zirconium, and zinc or any mixtures of said salts.

Particularly preferred active antiperspirant substances are selected from aluminum chlorohydrates, for example, aluminum sesquichlorohydrate, aluminum chlorhydrex propylene glycol (PG) or polyethylene glycol (PEG), aluminum sesquichlorhydrex PG or PEG, aluminum PG dichlorhydrex or aluminum PEG dichlorhydrex, aluminum hydroxide, further selected from aluminum zirconium chlorohydrates, such as aluminum zirconium trichlorohydrate, aluminum zirconium tetrachlorohydrate, aluminum zirconium pentachlorohydrate, aluminum zirconium octachlorohydrate, aluminum-zirconium-chlorohydrate-glycine complexes such as aluminum zirconium trichlorohydrex glycine, aluminum zirconium tetrachlorohydrex glycine, aluminum zirconium pentachlorohydrex glycine, aluminum zirconium octachlorohydrex glycine, aluminum undecylenoyl collagen amino acid, potassium aluminum sulfate, sodium aluminum lactate, aluminum sulfate, sodium aluminum chlorohydroxy lactate, aluminum bromohydrate, aluminum chloride, complexes of zinc and sodium salts, complexes of lanthanum and cerium, aluminum salts of lipoamino acids, aluminum sulfate, aluminum lactate, aluminum chlorohydroxy allantoinate, sodium aluminum chlorohydroxy lactate, zinc chloride, zinc sulfocarbolate, zinc sulfate, and zirconium chlorohydrate.

"Water solubility" of the active antiperspirant substances is understood to be a solubility of at least 5% by weight at 20° C., i.e., that amounts of at least 5 g of the active antiperspirant substance are soluble in 95 g of water at 20° C.

Particularly preferred are astringent aluminum salts, in particular aluminum chlorohydrate, which is marketed, for example, in powder form as Micro Dry® (Reheis (Interorgana)), in the form of an aqueous solution as Locron® L by Clariant, as Chlorhydrol® and in activated form as Reach® 103 or AACH® 7172 by Summit.

An aluminum sesquichlorohydrate is offered by Summit under the name Reach® 301. The use of aluminum-zirconium-trichlorohydrex-glycine complexes, which are commercially available, for example, from Summit under the name AAZG® 531 or AAZG® 531D, can also be particularly advantageous.

The active antiperspirant substances can also be used as aqueous solutions.

Other preferred active cosmetic substances within this embodiment are active deodorant substances, which are selected particularly preferably from odor absorbers, ion exchangers having a deodorizing action, bacteriostatic agents, prebiotically active components, and enzyme inhibitors or, particularly preferably, combinations of the aforesaid active substances.

Silicates serve as odor absorbers that simultaneously can also advantageously support the rheological properties of the compositions within this embodiment. The particularly advantageous silicates include primarily phyllosilicates and of these in particular montmorillonite, kaolinite, illite, beidellite, nontronite, saponite, hectorite, bentonite, smectite, and talc. Other advantageous odor absorbers are, for example, zeolites, zinc ricinoleate, cyclodextrins, certain metal oxides, such as, e.g., aluminum oxide, and chlorophyll.

Preferred as bacteriostatic or antimicrobial active substances are, in particular organohalogen compounds as well as organohalides, quaternary ammonium compounds, and a number of plant extracts and zinc compounds. These include, among others, triclosan, chlorhexidine and chlorhexidine gluconate, 3,4,4'-trichlorocarbanilide, bromochlorophene, dichlorophene, chlorothymol, chloroxylenol, hexachlorophene, dichloro-m-xylenol, dequalinium chloride, domiphen bromide, ammonium phenol sulfonate, benzalkonium halides, benzalkonium cetyl phosphate, benzalkonium saccharinate, benzethonium chloride, cetylpyridinium chloride, laurylpyridinium chloride, lauryl isoquinolinium bromide, and methylbenzedonium chloride.

Furthermore, also usable with preference are phenol, aryl alcohols such as, in particular phenoxyethanol, 2-methyl-4-phenylbutan-2-ol, and 2-methyl-5-phenylpentan-1-ol, disodium dihydroxyethyl sulfosuccinyl undecylenate, sodium bicarbonate, zinc lactate, sodium phenolsulfonate, and zinc phenolsulfonate, ketoglutaric acid, terpene alcohols such as, e.g., farnesol, chlorophyllin-copper complexes, alpha-monoalkylglycerol ethers having a branched or linear, saturated or unsaturated, optionally hydroxylated C6-C22 alkyl group, particularly preferably alpha-(2-ethylhexyl)glycerol ether, available commercially as Sensiva® SC 50 (from Schülke & Mayr), carboxylic acid esters, in particular carboxylic acid monoesters of mono-, di-, and triglycerol (in particular glycerol monolaurate, diglycerol monocaprinate, diglycerol monolaurate, triglycerol monolaurate, and triglycerol monomyristate), lantibiotics, and plant extracts (e.g., green tea and components of linden blossom oil).

Further preferred active deodorant substances can be selected from so-called prebiotically active components, which are to be understood as those components that inhibit only or at least predominantly the odor-forming microbes of the skin microflora, but not the desirable microbes, i.e. the non-odor-forming microbes. Explicitly included herein are the active substances that are disclosed in the German unexamined patent applications DE 10333245 and DE 102004011968 as being prebiotically active; these include conifer extracts, in particular from the Pinaceae group, and plant extracts from the group of the Sapindaceae, Araliaceae, Lamiaceae, and Saxifragaceae, in particular extracts from *Picea* spp., *Paullinia* sp., *Panax* sp., *Lamium album*, or *Ribes nigrum*, as well as mixtures of said substances.

Further preferred active deodorant substances can be selected from the perfume oils having a bacteriostatic effect and from the Deosafe perfume oils that can be obtained from the Symrise company.

The enzyme inhibitors include substances that inhibit the enzymes responsible for the decomposition of perspiration, in particular arylsulfatase, beta-glucuronidase, aminoacylase, ester-cleaving lipases, and lipoxygenases, e.g., trialkylcitric acid esters, in particular triethyl citrate, or zinc glycinate.

The active deodorant substances can be used both individually and in mixtures. Particularly preferred are phenoxyethanol, alpha-(2-ethylhexyl)glycerol ether, diglycerol monocaprinate, 2-methyl-4-phenylbutan-2-ol, mixtures of phenoxyethanol and alpha-(2-ethylhexyl)glycerol ether, and mixtures of aryl alcohols, in particular phenoxyethanol, with alpha-(2-ethylhexyl)glycerol ether and diglycerol monocaprinate, in particular mixtures of alpha-(2-ethylhexyl)glycerol ether and 2-methyl-5-phenylpentan-1-ol.

The total amount of active deodorant substances in the compositions of this embodiment is preferably 0.01-10% by weight, particularly preferably 0.1-7% by weight, in particular 0.2-5% by weight, and exceptionally preferably 0.3-1.0% by weight, based in each case on the total weight of the composition.

Within this embodiment, it can be of advantage, furthermore, if the compositions of the invention comprise in addition at least one propellant and an aerosol dispensing device, the parts of the dispensing device valves coming into contact with the composition preferably consisting of non-metallic materials.

Suitable propellants (propellant gases) are propane, propene, n-butane, isobutane, isobutene, n-pentane, pentene, isopentane, isopentene, methane, ethane, dimethyl ether, nitrogen, air, oxygen, laughing gas, 1,1,1,3-tetrafluoroethane, heptafluoro-n-propane, perfluoroethane, monochlorodifluoromethane, 1,1-difluoroethane, namely, both individually and also in combination. Hydrophilic propellant gases such as, e.g., carbon dioxide, can also be used advantageously in the context of the present invention, if the proportion of hydrophilic gases is selected as low and a lipophilic propellant gas (e.g., propane/butane) is present in excess.

Propane, n-butane, isobutane, and mixtures of said propellant gases are particularly preferred. Particularly preferred are propane/n-butane mixtures in the weight ratio of 10:90, preferably of 20:80.

The compositions of this embodiment and the propellant(s) are preferably filled into suitable aerosol containers in a weight ratio of 1:10 to 2:1, preferably of 1:7 to 1:1, and in particular of 1:5 to 1:2.

Vessels made of metal (aluminum, tin plate, tin), protected or non-splintering plastic or of glass that is externally coated with plastic may be used as compressed-gas containers; pressure resistance and breaking strength, corrosion resistance, ease of filling, as well as aesthetic aspects, handling, printability, etc., play a role in their selection. Special protective interior coatings assure corrosion resistance.

In another preferred embodiment, the compositions of the invention furthermore can include at least one fragrance component. Individual fragrance compounds, e.g., synthetic products of the ester, ether, aldehyde, ketone, alcohol, and hydrocarbon types, can be used as fragrances or perfume oils. Odorant compounds of the ester type are, for example, phenoxyethyl isobutyrate, benzyl acetate, p-tert-butylcyclohexyl acetate, dimethylbenzylcarbinyl acetate, linalyl acetate, phenylethyl acetate, linalyl benzoate, ethylmethylphenyl glycinate, benzyl formate, allylcyclohexyl propionate, styrallyl propionate, and benzyl salicylate. The ethers include, for example, benzylethyl ether; the aldehydes, for example, the linear alkanals having 8 to 18 C atoms, citral, citronellal, citronellyl oxyacetaldehyde, cyclamenaldehyde, hydroxycitronellal, lilial, and bourgeonal; the ketones, for example, the ionones alpha-isomethylionone and methylcedrylketone; the alcohols, anethol, citronellol, eugenol, geraniol, linalool, phenylethyl alcohol, and terpineol; the hydrocarbons include primarily terpenes and balsams. Preferably, however, mixtures of different fragrances are used, which together produce an attractive scent note. Suitable perfume oils can also include natural fragrance mixtures, as are obtainable from plant or animal sources, e.g., pine, citrus, jasmine, lily, rose, or ylang ylang oil. Essential oils with a low volatility, which are mainly used as aroma components, are also suitable as perfume oils, e.g., sage oil, chamomile oil, clove oil, melissa oil, mint oil, cinnamon leaf oil, lime blossom oil, juniper berry, vetiver oil, olibanum oil, galbanum oil, and laudanum oil.

The fragrance component(s) can be used in the compositions of the invention preferably in total amounts of 0 to 5% by weight, particularly preferably 0.1 to 4% by weight, and in particular of 0.5 to 3% by weight, based in each case on the weight of the compositions.

A second subject of the present invention is the cosmetic, nontherapeutic use of the cosmetic composition of the invention to treat excessive pigmentation, pigmentation disorders, age spots, and/or post-inflammatory hyperpigmentation of the skin.

A third subject of the invention is a method for producing a cosmetic skin-bleaching composition in the form of an O/W or a W/O emulsion, in which an oily extract from licorice roots is dissolved in the aqueous phase by the addition of an ascorbic acid ester.

Methods particularly preferred according to the invention are characterized in that an isopropyl myristate extract from licorice roots is combined in the aqueous phase with ascorbyl tetraisopalmitate.

Because of the combination, the oily plant extract is completely dissolved in the aqueous phase of the emulsion.

Examples

1) Synergistic Effect of Licorice Extract (Oil-Soluble) and Ascorbic Acid Ester

The effect of licorice extract (oil-soluble) and ascorbyl tetraisopalmitate on the expression of melanogenesis-relevant genes was studied in reconstructed melanocyte models type VI from the company Skinethic. In this case, human keratinocytes were cultured together with type VI melanocytes, so that a very dark skin model forms. Together the cells form a three-dimensional epithelial tissue. Three models each were treated topically for 24 hours with 30 µL of the test formulations. In this case, the formulation is first applied to the model and then carefully distributed with a brush. Incubation then occurs at 37° C. with 5% $CO_2$. Untreated models and models treated with a blank control (3% PEG-40 Hydrogenated Castor Oil in water) were run concurrently as the control. The gene expressions of the melanocyte-specific markers were studied using quantitative real-time PCR. To carry out the PCR, first with use of the RNeasy Mini Kit from the company Qiagen, the RNA from the melanocyte models is isolated and transcribed into cDNA by reverse transcription. In the subsequent PCR reaction, which is carried out with the aid of gene-specific primers for the particular markers and is used for the amplification of the target gene segments, the formation of the PCR products is detected online via a fluorescence signal. The fluorescence signal in this case is proportional to the amount of the formed PCR product. The greater the expression of a specific gene, the greater the amount of the formed PCR product and the greater the fluorescence signal. The gene expression of the gene to be determined is designated by a plus as an increased expression in comparison with the blank control or with a minus as a decreased expression (Table 1).

Various melanogenesis-associated parameters were studied:
- ckit: ckit is the receptor for the growth factor SCF. SCF has a cell division-stimulating effect on the melanocytes via coupling to the receptor. If the receptor expression is reduced, the stimulating action of SCF can be inhibited.
- gp100: gp100 codes for a protein of the melanosome membrane, in which the melanin produced by melanocytes is transferred to the keratinocytes. The melanin transfer can be reduced by inhibiting this gene.
- TRP1 and 2: TRP1 and 2 as enzymes play an important role in the enzymatic conversion of tyrosine to melanin during melanin synthesis.
- Tyr: Tyrosinase is the initially necessary enzyme, which catalyzes the first step in the conversion of tyrosine to melanin.

TABLE 1

|  | ckit | Gp100 | TRP1 | TRP2 | Tyr |
|---|---|---|---|---|---|
| 0.5% Licorice extract (oil-soluble) | − | − | + | + | − |
| 0.05% Vitamin tetraisopalmitate | 0 | − | − | + | + |
| 0.5% Licorice extract (oil-soluble) + 0.05% ascorbyl tetraisopalmitate | − | − | 0 | − | − |

Table 1 shows the gene expression of various formulations. The substances were tested in water, including 3% by weight of PEG-40 Hydrogenated Castor Oil. The gene expression is shown in comparison with the blank control. Here:
+ stands for increased expression
− for reduced expression
0 for no change.

The data shows that a satisfactory and consistent change in gene expression within the context of reduced new formation of melanin has occurred only with the combination of the two active substances, licorice extract (oil-soluble) and ascorbyl tetraisopalmitate.

2) Insufficient Action of Licorice Extract (Water-Soluble)

In a further test, skin models of the SkinEthic type (company SkinEthic, France) including keratinocytes and melanocytes were incubated for 8 days with a formulation including 1% of a water-soluble licorice extract. The melanin content was determined by spectrophotochemistry. No reduction of the melanin content in comparison with the blank control could be demonstrated.

3) Exemplary Embodiments a) Antiperspirant Roll-on (Quantitative Data Given in % by Weight)

TABLE 2

|  | A | B | C | D |
|---|---|---|---|---|
| PPG-15 stearyl ether | 0.50 | 0.50 | 0.50 | 0.50 |
| Steareth-2 | 2.38 | 2.38 | 2.38 | 2.38 |
| Steareth-21 | 1.48 | 1.48 | 1.48 | 1.48 |
| Aluminum chlorohydrate (50% in water) | 40.00 | 40.00 | 40.00 | 40.00 |
| Talc | 0.30 | 0.30 | 0.30 | 0.30 |
| Herbasol Extract Liquorice ®[1] IPM | 0.50 | 1.00 | 2.00 | 0.50 |
| Nikkol ®[2] VC IP | 0.05 | 0.10 | 0.20 | 0.05 |
| Allantoin | 0.10 | 0.30 |  | 0.20 |
| Alpha-Bisabolol |  |  | 0.20 |  |
| EDTA BX ®[3] Powder | 0.10 | 0.10 | 0.10 | 0.10 |
| Perfume | 0.65 |  | 0.50 |  |
| Water | To 100 | To 100 | To 100 | To 100 |

List of Raw Materials Employed:

1 INCI name: Isopropyl Myristate, *Glycyrrhiza Glabra* (Licorice) Root Extract; Cosmetochem 2 INCI name: Ascorbyl Tetraisopalmitate; Nikko Chemicals 3 INCI name: Tetrasodium EDTA; BASF b) Antiperspirant Aerosol (Quantitative Data Given in % by Weight)

TABLE 3

|  | A | B | C |
|---|---|---|---|
| Xiameter PMX-0245 ®[4] | 10.70 | 10.70 | 10.70 |
| Dow Corning ES-5227 ®[5] DM | 5.60 | 5.60 | 5.60 |
| Isopropyl myristate | 6.60 | 6.60 | 6.60 |
| Propylene glycol | 23.40 | 23.40 | 23.40 |
| Phenoxyethanol | 0.50 | 0.50 | 0.50 |
| Aluminum chlorohydrate (50% in water) | 50.00 | 50.00 | 50.00 |
| Herbasol Extract Liquorice ®[1] IPM | 1.00 | 2.00 | 0.50 |
| Nikkol ®[2] VC IP | 0.10 | 0.20 | 0.05 |
| Allantoin | 0.10 |  | 0.20 |
| Alpha-Bisabolol |  | 0.20 |  |
| Perfume | 2.50 | 2.50 | 2.50 |
| Water | To 100 | To 100 | To 100 |

Formulations A, B, and C are each filled into aerosol containers in the weight ratio of 1:4 with the propellant propane/n-butane (20/80).

List of Raw Materials Employed
4 INCI name: Cyclomethicone; Dow Corning
5 INCI name: Dimethicone, PEG/PPG-18/18 Dimethicone; Dow Corning The compositions given under a) and b) have an excellent skin tolerance. They are stable, show no separation effects, and result in a smooth, well-cared-for skin. After repeated use, a significant lightening of the treated skin area could be demonstrated.

While at least one exemplary embodiment has been presented in the foregoing detailed description of the invention, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing an exemplary embodiment of the invention, it being understood that various changes may be made in the function and arrangement of elements described in an exemplary embodiment without departing from the scope of the invention as set forth in the appended claims and their legal equivalents.

What is claimed is:

1. A cosmetic composition for skin bleaching, comprising
a) at least one oily plant extract from a root of *Glycyrrhiza glabra* using isopropyl myristate as the extracting agent, and
b) ascorbyl tetraisopalmitate,
wherein the weight ratio of components a) to b) is 10:1.

2. The cosmetic composition according to claim 1, wherein the ascorbyl tetraisopalmitate b) comprises 0.005 to 1% by weight in terms of the total weight of the composition.

3. The cosmetic composition according to claim 1, wherein the ascorbyl tetraisopalmitate b) comprises 0.01 to 0.2% by weight in terms of the total weight of the composition.

4. The cosmetic composition according to claim 1, further comprising allantoin in a weight proportion of 0.01 to 5% by weight based on the total weight of the composition.

5. The cosmetic composition according to claim 1, further comprising allantoin in a weight proportion of 0.1 to 1% by weight based on the total weight of the composition.

6. The cosmetic composition according to claim 1, further comprising at least one silicone in a weight proportion of 0.05 to 20% by weight based on the total weight of the composition.

7. The cosmetic composition according to claim 1, further comprising at least one silicone in a weight proportion of 0.5 to 12.5% by weight based on the total weight of the composition.

8. The cosmetic composition according to claim 1, further comprising at least one active antiperspirant substance in a weight proportion of 3 to 40% by weight based on the total weight of the composition.

9. The cosmetic composition according to claim 1, wherein the composition is in the form of a solution, an emulsion of a water-in-oil (W/O) or oil-in-water (O/W) type, a multiple emulsion of a water-in-oil-in-water (W/O/W) or oil-in-water-in-oil (O/W/O) type, a hydrodispersion or lipid dispersion, a gel, a solid stick, and/or an aerosol.

* * * * *